US006911548B2

(12) United States Patent
Petersen

(10) Patent No.: US 6,911,548 B2
(45) Date of Patent: Jun. 28, 2005

(54) METHOD FOR THE PREPARATION OF 5-CYANOPHTHALIDE

(75) Inventor: Hans Petersen, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/191,808

(22) Filed: Jul. 8, 2002

(65) Prior Publication Data

US 2003/0013895 A1 Jan. 16, 2003

Related U.S. Application Data

(63) Continuation of application No. PCT/DK00/00016, filed on Jan. 14, 2000.

(51) Int. Cl.$^7$ .................... C07D 307/87; C07D 307/88
(52) U.S. Cl. ........................ 549/307; 549/467
(58) Field of Search .................. 549/307, 467

(56) References Cited

U.S. PATENT DOCUMENTS

| | | | |
|---|---|---|---|
| 3,467,675 A | 9/1969 | Petersen et al. ......... | 260/346.2 |
| 4,136,193 A | 1/1979 | Bogeso et al. ........... | 424/285 |
| 4,650,884 A | 3/1987 | Bogeso .................... | 549/467 |
| 4,943,590 A | 7/1990 | Boegesoe et al. ........ | 415/469 |
| 5,296,507 A | 3/1994 | Tanaka et al. ........... | 514/465 |
| 6,020,501 A | 2/2000 | Massonne et al. ....... | 549/307 |
| 6,028,204 A | 2/2000 | Massonne et al. ....... | 549/307 |
| 6,229,026 B1 | 5/2001 | Petersen ................... | 549/467 |
| 6,258,842 B1 | 7/2001 | Petersen et al. ......... | 514/469 |
| 6,291,689 B1 | 9/2001 | Petersen et al. ......... | 549/467 |
| 6,310,222 B1 | 10/2001 | Ikemoto et al. .......... | 549/467 |
| 6,365,747 B1 | 4/2002 | Dall'Asta et al. ....... | 548/146 |
| 6,392,060 B2 | 5/2002 | Petersen et al. ......... | 549/307 |
| 6,403,813 B1 | 6/2002 | Petersen et al. ......... | 549/305 |
| 6,407,267 B1 | 6/2002 | Rock et al. .............. | 549/467 |
| 6,420,574 B2 | 7/2002 | Petersen et al. ......... | 549/467 |
| 6,426,422 B1 | 7/2002 | Petersen et al. ......... | 549/467 |
| 2002/0004604 A1 | 1/2002 | Petersen et al. ......... | 549/462 |
| 2002/0026062 A1 | 2/2002 | Petersen et al. ......... | 549/467 |
| 2002/0028956 A1 | 3/2002 | Weber ...................... | 549/307 |
| 2002/0035277 A1 | 3/2002 | Rock et al. .............. | 549/467 |
| 2002/0040153 A1 | 4/2002 | Petersen ................... | 549/467 |
| 2002/0061925 A1 | 5/2002 | Petersen et al. ......... | 514/469 |
| 2002/0077353 A1 | 6/2002 | Petersen et al. ......... | 514/469 |
| 2002/0087012 A1 | 7/2002 | Castellin et al. ......... | 549/467 |

FOREIGN PATENT DOCUMENTS

| | | | | |
|---|---|---|---|---|
| EP | 0 171 943 A1 | 2/1986 | ......... | C07C/121/80 |
| EP | 1 095 926 | 5/2001 | ........... | C07C/33/46 |
| WO | 98/19511 | 5/1998 | | |
| WO | 98/19512 | 5/1998 | | |
| WO | 98/19513 | 5/1998 | | |
| WO | 99/30548 | 6/1999 | | |
| WO | 00/11926 | 3/2000 | | |
| WO | 00/12044 | 3/2000 | | |
| WO | 00/13648 | 3/2000 | | |
| WO | 00/23431 | 4/2000 | ......... | C07D/307/87 |
| WO | 00/39112 | 7/2000 | ......... | C07D/307/87 |
| WO | 00/44738 | 8/2000 | ......... | C07D/307/88 |
| WO | 01/45483 | 6/2001 | | |
| WO | 01/47877 | 7/2001 | | |
| WO | 01/47909 | 7/2001 | ......... | C07D/307/87 |
| WO | 01/49672 | 7/2001 | ......... | C07D/307/87 |
| WO | 01/51477 | 7/2001 | ......... | C07D/307/87 |
| WO | 01/66536 | 9/2001 | ......... | C07D/307/87 |

OTHER PUBLICATIONS

U.S. Appl. No. 10/186,337, filed Jun. 27, 2002.
U.S. Appl. No. 10/183,958, filed Jun. 25, 2002.
Levy, L.F., "4–Aminophthalide and Some Derivatives", *J. Chem. Soc.* pp. 867–870 (1931).
Tirouflet J., "Phtalide Substitues en 5", *Bull. Soc. Sci. de Bretagne* 26:35–43 (1951).
Bigler, Allan et al., "Quantitative Structure–activity Relationships in a Series of Selective 5–HT uptake inhibitors," *Eur. J. Med. Chem.* 3:289–295 (1997).
Forney L., "Reaction of Terephthalic Acid with Formaldehyde in Sulfur Trioxide Media," *J. Org. Chem.* 35:1695–1696 (1970).
Dordor et al., "Reaction of Oxazolines with Phosphorus Oxychloride," *Tetrahedron Letters* 24:1437–1440 (1983).
Barton et al., *Comprehensive Organic Chemistry. The Synthesis and Reactions of Organic Compounds*, vol. 2, pp. 1024–1025, Year Not Available.
Isabelle M. Dordor et al., "Reaction of oxazolines with phosphorous oxychloride," *Tetrahedron Letters* 24, 13: 1437–1440 (1983).

*Primary Examiner*—Laura L. Stockton
(74) *Attorney, Agent, or Firm*—Darby & Darby

(57) ABSTRACT

A method for the preparation of 5-cyanophthalide comprising treatment of a compound of formula IV formula IV

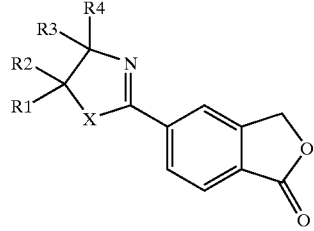

wherein X is O or S;

$R^1$–$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring; with a dehydration agent or alternatively where X is S, thermally cleavage of the thiazoline ring or treatment with a radical initiator, such as peroxide or with light, to form 5-cyanophthalide, which is an important intermediate used in the preparation of the antidepressant drug citalopram.

32 Claims, No Drawings

METHOD FOR THE PREPARATION OF 5-CYANOPHTHALIDE

This application is a continuation of International application no. PCT/DK00/00016, filed Jan. 14, 2000. The prior application is hereby incorporated by reference, in its entirety.

The present invention relates to a novel process for the preparation of 5-cyanophthalide which is an intermediate used for the manufacture of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

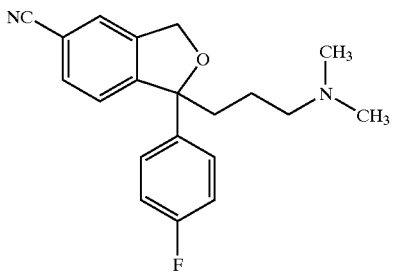

Formula I

It is a selective, centrally active serotonin (5-hydroxytryptamine; 5-HT) reuptake inhibitor, accordingly having antidepressant activities. The antidepressant activity of the compound has been reported in several publications, e.g. J. Hyttel, *Prog. Neuro-Psychopharmacol. & Biol. Psychiat.*, 1982, 6, 277–295 and A. Gravem, *Acta Psychiatr. Scand.*, 1987, 75, 478–486.

Citalopram is prepared by the process described in U.S. Pat. No. 4,650,884, according to which 5-cyanophthalide is subjected to two successive Grignard reactions, i.e. with 4-fluorophenyl magnesium halogenide and N,N-dimethylaminopropyl magnesium halogenide, respectively, and the resulting compound of the formula

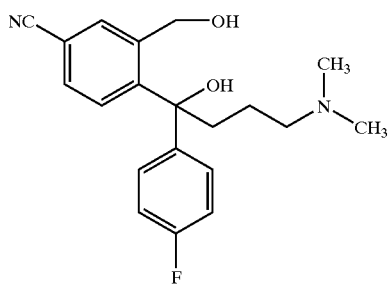

Formula II is subjected to a ring closure reaction by dehydration with strong sulfuric acid.

Enantiomers of citalopram may be prepared by the method described in U.S. Pat. No. 4,943,590, i.e. by separating the enantiomers of the intermediate of Formula II and performing enantioselective ring closure in order to obtain the desired enantiomer.

Thus, 5-cyanophthalide is an important intermediate for the manufacture of citalopram and it is important to produce this material in an adequate quality, by a convenient process and in a cost-effective way.

A method for the preparation of 5-cyanophthalide has previously been described in *Bull. Soc. Sci. Bretagne,* 1951, 26, 35 and in Levy and Stephen, *J. Chem. Soc.,* 1931, 867. By this method 5-aminophthalide is converted to the corresponding 5-cyanophthalide by diazotation followed by reaction with CuCN. 5-Aminophthalide was obtained from 4-aminophthalimide by a two step reduction procedure.

Synthesis of certain alkyl- and phenylnitriles from acid chlorides is described in *Tetrahedron Letters,* 1982, 23, 14, 1505–1508, and in *Tetrahedron,* 1998, 54, 9281.

It has been found that 5-cyanophthalide may be prepared in high yields by a convenient, cost-effective procedure from the 2-(1-oxo-1,3-dihydroisobenzofuran-5-yl)oxazoline or -thiazoline intermediates of Formula IV.

DESCRIPTION OF THE INVENTION

Accordingly, the present invention provides a novel method for the preparation of 5-cyanophthalide comprising treatment of a compound of Formula IV

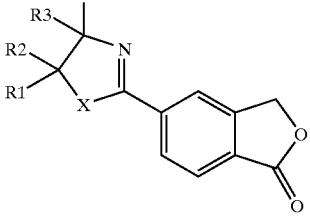

Formula IV wherein X is O or S;

$R^1$–$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring;

with a dehydration agent or alternatively where X is S, by thermal cleavage of the thiazoline ring or treatment with a radical initiator, such as peroxide or with light, to form 5-cyanophthalide having the formula

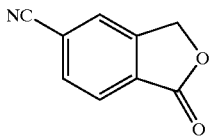

Formula III

The dehydration agent may be phosphoroxytrichloride, thionylchloride, phosphorpentachloride, PPA (polyphosphoric acid), and $P_4O_{10}$. The reaction may be carried out in the presence of an organic base, such as pyridine or a catalytic amount of a tertiary amide.

Preferably, the compound of Formula IV is treated with $SOCl_2$ as a dehydrating agent and the reaction is carried out in toluene comprising a catalytic amount of N,N-dimethylformamide.

Alternatively, the dehydration agent may be a Vilsmeier reagent, i.e. a compound which is formed by reaction of a chlorinating agent, preferably an acid chloride, e.g. phosgene, oxalyl chloride, thionyl chloride, phosphoroxychloride, phosphorpentachloride, trichloromethyl chloroformate, also briefly referred to as "diphosgene", or bis(trichloromethyl) carbonate, also briefly referred to as "triphosgene", with a tertiary amide such as N,N-dimethylformamide or a N,N-dialkylalkanamide, e.g. N,N-dimethylacetamide. A classic Vilsmeier reagent is the chloromethylenedimethyliminium chloride. The Vilsmeier reagent is preferably prepared in situ by adding the chlorinating agent to a mixture containing the starting oxazoline or thiazoline derivative of formula IV and the tertiary amide.

When X is S and the conversion of the thiazoline group into the cyano group is made by thermal transformation, the thermal decomposition of compound IV is preferably carried out in an anhydrous organic solvent, more preferably an aprotic polar solvent, such as N,N-dimethylformamide, N,N-dimethylacetamide, dimethylsulfoxide or acetonitrile. The temperature at which the thermal decomposition transforms the 2-thiazolyl group to a cyano group is between 60° C. and 140° C. The thermal decomposition may conveniently be carried out by reflux in a suitable solvent, preferably acetonitrile. The thermal cleavage may conveniently be carried out in the presence of oxygen or an oxidation agent. Compounds of Formula IV where X is S and $R^4$ is a carboxy group or a precursor for a carboxy group can also be converted to citalopram by treatment with a radical initiator such as light or peroxides.

Throughout the specification and the claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Accordingly, by the process of the invention, 5-cyanophthalide is obtained in high yields and the process is much more convenient than the known process. It is a so-called robust process. The usage of CuCN is eliminated thereby minimising the amount of undesirable by-products and making an environmentally compatible process.

In a further aspect, the invention relates to a method for preparing the intermediate of Formula IV comprising:

a) reacting a functional derivative of 5-carboxyphthalide of Formula V

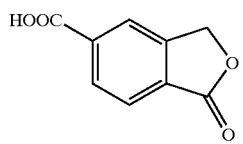

Formula V with a 2-hydroxy- or 2-mercaptoethanamine of Formula VI

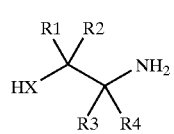

Formula VI in which X, $R^1$–$R^4$ are as defined above, (b) submitting the amide of Formula VII thus obtained

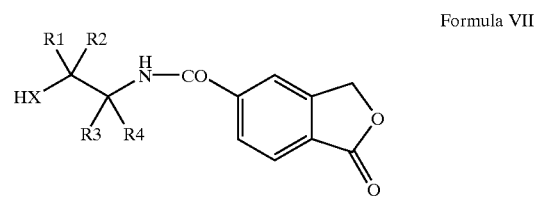

Formula VII in which X, $R^1$–$R^4$ are as defined above, to a ring closure by dehydration; thereby obtaining the 2-(1-oxo-1,3-dihydroisobenzofuran-5-yl)oxazoline or -thiazoline of Formula IV

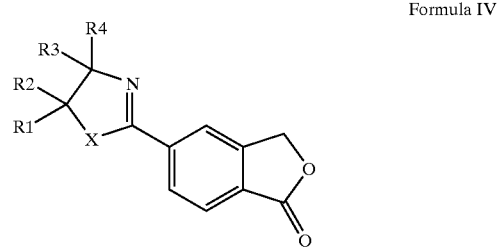

Formula IV

Preferably, the functional derivative used in step a) is an ester, such as alkylester, arylester or alkylarylester derivative of 5-carboxyphthalide, or an acidhalide derivative of 5-carboxyphthalide.

Preferably, the dehydrating agent used in step b) is $SOCl_2$, $POCl_3$ and $PCl_5$, most preferably $SOCl_2$.

The reaction in step b) is carried out neat or in a suitable solvent, such as toluene, sulfolan or acetonitrile. Furthermore, when a solvent is used, a catalytic amount of N,N-dimethylformamide may be needed, in particular when the dehydrating agent is $SOCl_2$. Preferably, toluene is used as the solvent, if necessary in the presence of a catalytic amount of N,N-dimethylformamide.

The reaction in step b) is carried out at elevated temperature, preferably at the reflux temperature of the solvent.

The reaction time is not important and may easily be determined by a person skilled in the art.

The 5-carboxyphthalide used as a starting material may be obtained by the methods described in U.S. Pat. No. 3,607,884 or German Patent No. 2630927, i.e. by reacting a concentrated solution of terephthalic acid with formaldehyde in liquid $SO_3$ or by electrochemical hydrogenation of trimellithic acid.

In a preferred embodiment of the process of the invention, $R^3$ is methyl or ethyl.

5-Cyanophthalide may be isolated in a conventional way, e.g. by addition of water, filtration and subsequent washing of the crystals. Further purification may, if desired, be performed by recrystallisation.

Accordingly, by the process of the invention, 5-cyanophthalide is obtained by the novel use of the 2-(1-oxo-1,3-dihydroisobenzofuran-5-yl)oxazoline or -thiazoline intermediates of Formula IV as reactants. Using these reactants, process conditions are much more convenient than the conditions previously described in the known process for preparing 5-cyanophthalide, especially with the use of $SOCl_2$ as a dehydrating agent.

EXAMPLES

The invention is further illustrated by the following examples.

Example 1

Preparation of 2-[[(1-oxo-1,3-dihydroisobenzofuran-5-yl)carbonyl]amino]-2-methyl-1-propanol.

5-carboxyphthalide (267 g, 1.5 mol) is added to thionyl chloride (950 mL) and then N,N-dimethylformamide (12 mL) is added dropwise. The mixture is heated at reflux for 1 hour and the thionyl chloride is destined off under reduced pressure followed by successive evaporations with toluene (2×50 mL) to give a solid residue. The crude acid chloride is then taken up with 1000 mL of tetrahydrofuran. To a solution of 2-amino-2-methyl-1-propanol (400.5 g, 4.5 mol) in tetrahydrofuran (500 mL), cooled to +5° C. chloride solution is added dropwise whilst maintaining the temperature between +5→+10° C. After the addition is completed, the cooling is removed and the mixture is stirred overnight at ambient temperature. Then the mixture is poured into deionized water (2000 mL) and the organic solvent is removed under reduced pressure at 50° C. After cooling and stirring for 2 hours, the solid product is filtered off and washed with deionized water (2×100 mL). The obtained product is dried at 70° C. for 36 hours under reduced pressure. Yield: 285.3 g (76%) of an off-white product having a purity (HPLC, peak area)=90%. $^1$H NMR (DMSO d-6, 500 MHz): 1.18 (3H, s), 1.32 (3H, s), 3.55 (2H, s), 5.45 (2H, s), 7.88–7.98 (3H, m), 8.07 (1H, s).

Example 2

Preparation of 4,4-dimethyl-2-(1-oxo-1,3-dihydroisobenzofuran-5-yl)oxazoline.

To thionyl chloride (130 ml), cooled at −10° C., 2-[[(1-oxo-1,3-dihydroiso-benzofuran-5-yl)carbonyl]amino]-2-methyl-1-propanol (85 g, 0.34 mol) is added portionwise with stirring. The temperature is maintained at −10→−5° C. for 1.5 hours whereafter the cooling is removed and the reaction is stirred overnight at ambient temperature. It is then cooled to 0° C. and tetrahydrofuran (860 mL) is added dropwise keeping the temperature below +8° C. The obtained suspension is kept under stirring for 2 hours at 5° C., and then filtered and the crystals washed with tetrahydrofuran (150 mL). The wet solid is dissolved in deionized water (400 mL) and the pH is adjusted to 9.1 by the addition of 25% aqueous ammonia. The solid is filtered, washed with deionized water and dried for 14 hours at 50° C. under reduced pressure. Yield: 62.8 g (80%) of a white product having a purity (HPLC, peak area)=94%. $^1$H NMR (DMSO d-6, 500 MHz): 1.31 (6H, s), 4.18 (2H, s), 5.44 (2H, s), 7.9 (1H, d, J=11.3 Hz), 8.01 (1H, d, J=11.3 Hz), 8.12 (1H, s).

Example 3

Preparation of 5-cyanophthalide.

To a suspension of 4,4-dimethyl-2-(1-oxo-1,3-dihydroisobenzofuran-5-yl)oxazoline (23.1 g, 0.1 mol) in thionyl chloride (36 mL) is slowly added N,N-dimethylformamide (5 ml). The solution is heated at reflux for 1 hour and then allowed to cool to room temperature over 3 hours. Then toluene (150 mL) is added and the suspension is filtered and washed with toluene (2×50 mL). The wet crystals are taken into deionized water (150 mL) and the pH is adjusted to 8.0 with 25% aqueous ammonia. The solid is filtered and washed with deionized water (2×50 mL) and dried at 60° C. under reduced pressure. Yield: 11.9 g (75%) of an off-white product having a purity (HPLC, peak area)= 92%. An analytical pure sample is obtained by crystallisation from acetic acid or toluene. $^1$H NMR (DMSO d-6, 500 MHz): 5.48 (2H, s), 8.04 (2H, s+s), 8.22 (1H, s).

What is claimed is:

1. A method for the preparation of 5-cyanophthalide comprising reacting a compound of Formula IV

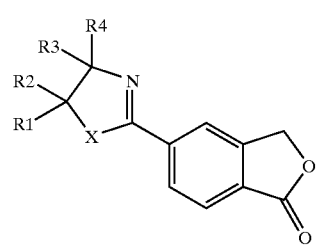

Formula IV wherein X is O or S;

$R^1$–$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or $R^3$ and $R^4$ together form a $C_{2-5}$ alkylene chain thereby forming a spiro-ring;

with a dehydration agent or alternatively where X is S, by thermal cleavage of the thiazoline ring or treatment with a radical initiator, to form 5-cyanophthalide having the formula

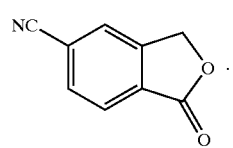

Formula III

2. The method of claim 1 wherein the compound of Formula IV is prepared by a process comprising:

a) reacting a 5-carboxyphthalide of Formula V

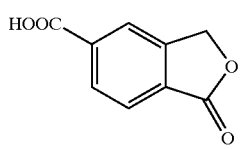

Formula V or an ester or acid halide derivative thereof with a 2-hydroxy- or 2-mercaptoethanamine of Formula VI

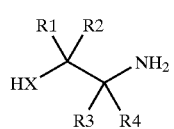

Formula VI in which X, $R^1$–$R^4$ are as defined in claim 1, (b) submitting the amide of Formula VII thus obtained

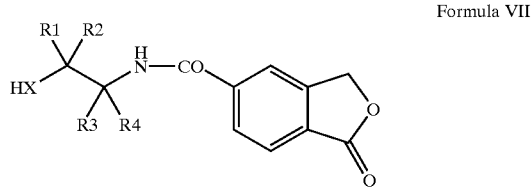
Formula VII in which X, $R^1$–$R^4$ are as defined in claim 1, to a ring closure by dehydration; thereby obtaining the 2-(1-oxo-1,3-dihydroisobenzofuran-5-yl)oxazoline or -thiazoline of formula IV

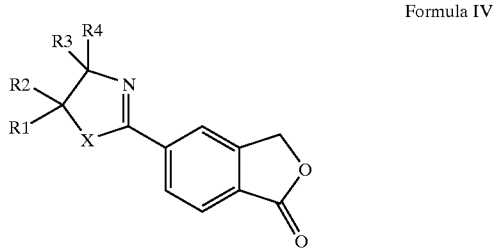
Formula IV in which X, $R^1$–$R^4$ are as defined in claim 1.

3. A method for the preparation of 5-cyanophthalide according to claim 1 or 2 wherein the compound of formula IV is reacted with a dehydrating agent selected from the group consisting of phosphoroxytrichloride, thionylchloride, phosphorpentachloride, PPA (polyphosphoric acid) and $P_4O_{10}$ or a Vilsmeier reagent, in combination with an organic base, or a catalytic amount of a tertiary amide.

4. The method of claim 3 wherein the reaction occurs in combination with an organic base, wherein said organic base is pyridine.

5. The method of claim 3 wherein the compound of formula IV is reacted with $SOCl_2$ as a dehydrating agent and the reaction is carried out in toluene comprising a catalytic amount of N,N-dimethylformamide.

6. A method for the preparation of 5-cyanophthalide according to claim 1 or 2 wherein the thermal cleavage of the thiazoline ring of a compound of formula IV where X is S is carried out in presence of oxygen or an oxidizing agent.

7. A method for the preparation of 5-cyanophthalide according to claim 1 or 2 wherein the thiazoline ring of a compound of formula IV where X is S and $R^4$ is carboxy is treated with a radical initiator.

8. The method of claim 1 wherein $R^3$ is methyl or ethyl.

9. The method of claim 2 wherein the dehydrating agent used in step b) is $SOCl_2$, $POCl_3$ or $PCl_5$.

10. The method of claim 9 wherein the dehydrating agent is $SOCl_2$.

11. The method of claim 2 wherein the reaction in step b) is carried out neat or in a solvent.

12. The method of claim 11, wherein the reaction in step b) is carried out in a solvent selected from the group consisting of toluene, sulfolan and acetonitrile.

13. The method of claim 9 wherein the dehydrating agent used in step b) is $SOCl_2$ and the reaction is carried out in toluene comprising a catalytic amount of N,N-dimethylformamide.

14. The method of claim 1 wherein X is S and the radical initiator is peroxide.

15. The method of claim 1 wherein X is S and the radical initiator is light.

16. A method for preparing Citalopram, having the formula

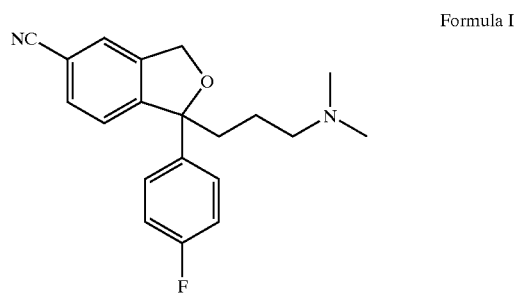
Formula I or an enantiomer thereof, said method comprising the preparation of 5-cyanophthalide by a process comprising reacting a compound of Formula IV

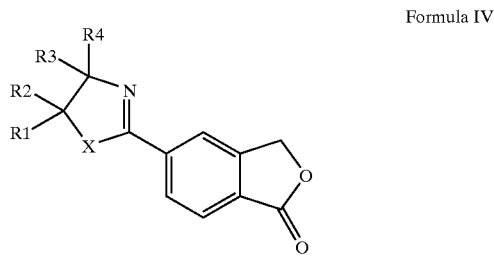
Formula IV wherein X is O or S;

$R^1$–$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, and a carboxy group, or $R^3$ and $R^4$ together form a $C_{2-5}$ alkylene chain thereby forming a spiro-ring;

with a dehydration agent or alternatively where X is S, by thermal cleavage of the thiazoline ring or treatment with a radical initiator, to form 5-cyanophthalide having the formula

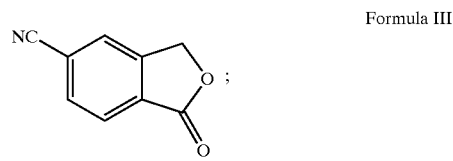
Formula III and converting the 5-cyanophthalide into Citalopram.

17. The method of claim 16 wherein the compound of Formula IV is prepared by a process comprising:

a) reacting a 5-carboxyphthalide of Formula V

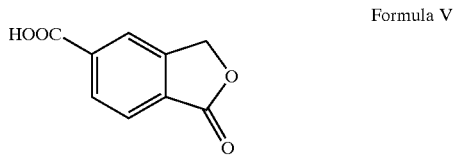
Formula V or an ester or acid halide derivative thereof with a 2-hydroxy- or 2-mercaptoethanamine of Formula VI

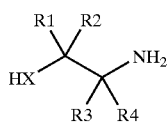

Formula VI in which X, R¹–R⁴ are as defined in claim 16,
(b) submitting the amide of Formula VII thus obtained

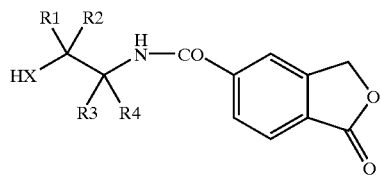

Formula VII in which X, R¹–R⁴ are as defined in claim 16, to a ring closure by dehydration;

thereby obtaining the 2-(1-oxo-1,3-dihydroisobenzofuran-5-yl)oxazoline or -thiazoline of formula IV

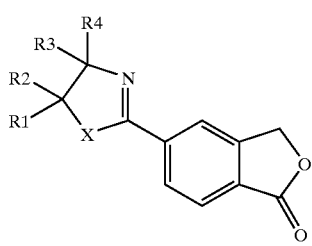

Formula IV in which X, R¹–R⁴ are as defined in claim 16.

18. The method for the preparation of Citalopram of claim 16 or 17 wherein the compound of formula IV is reacted with a dehydrating agent selected from the group consisting of phosphoroxytrichloride, thionylchioride, phosphorpentachloride, PPA (polyphosphoric acid) and $P_4O_{10}$ or a Vilsmeier reagent, in combination with an organic base, or a catalytic amount of a tertiary amide.

19. The method of claim 18 wherein the reaction occurs in combination with an organic base, wherein said organic base is pyridine.

20. The method of claim 18 wherein the compound of formula IV is reacted with $SOCl_2$ as a dehydrating agent and the reaction is carried out in toluene comprising a catalytic amount of N,N-dimethylformamide.

21. The method of claim 16 or 17 wherein the thermal cleavage of the thiazoline ring of a compound of formula IV where X is S is carried out in the presence of oxygen or an oxidizing agent.

22. The method of claim 16 or 17 wherein the thiazoline ring of a compound of formula IV where X is S and R⁴ is carboxy is treated with a radical initiator.

23. The method of claim 16 wherein R³ is methyl or ethyl.

24. The method of claim 17 wherein the dehydrating agent used in step b) is $SOCl_2$, $POCl_3$ or $PCl_5$.

25. The method of claim 24 wherein the dehydrating agent is $SOCl_2$.

26. The method of claim 17 wherein the reaction in step b) is carried out neat or in a solvent.

27. The method of claim 26 wherein the reaction in step b) is carried out in a solvent selected from the group consisting of toluene, sulfolan and acetonitrile.

28. The method of claim 17 wherein the dehydrating agent used in step b) is $SOCl_2$ and the reaction is carried out in toluene comprising a catalytic amount of N,N-dimethylformamide.

29. The method of claim 16 wherein X is S and the radical initiator is peroxide.

30. The method of claim 16 wherein X is S and the radical initiator is light.

31. The method of preparing Citalopram of claim 16, wherein said process further comprises the steps of reacting 5-cyanophthalide with 4-fluorophenyl magnesium halide and subsequently N,N-dimethylaminopropyl magnesium halide, to form compound (II)

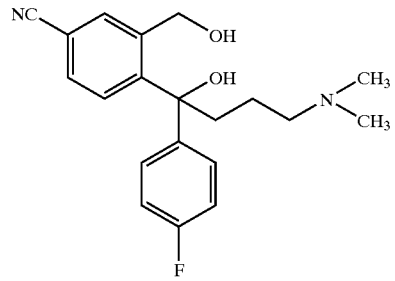

and subjecting compound (II) to ring closure to form Citalopram.

32. The method of preparing an enantiomer of Citalopram-of claim 16, wherein said process further comprises (a) reacting 5-cyanophthalide with 4-fluorophenyl magnesium halide and subsequently with N,N-dimethylaminopropyl magnesium halide to obtain the compound (II);

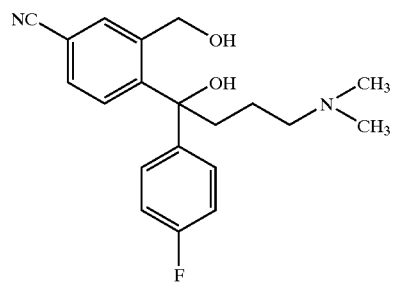

(b) separating the enantiomers of compound (II); and
(c) performing enantioseletive ring closure to obtain an enantiomer of Citalopram.

* * * * *